United States Patent [19]

Bacich et al.

[11] Patent Number: 5,279,280
[45] Date of Patent: Jan. 18, 1994

[54] ENDOSCOPE WITH GROOVED OUTER SURFACE

[75] Inventors: Steven R. Bacich, Laguna Niguel; Gary M. Woker, Escondido; Robert J. Elicker, La Habra, all of Calif.

[73] Assignee: Imagyn Medical, Inc., Laguna Niguel, Calif.

[21] Appl. No.: 4,103

[22] Filed: Jan. 13, 1993

Related U.S. Application Data

[63] Continuation-in-part of Ser. No. 780,871, Oct. 18, 1991.

[51] Int. Cl.⁵ ............................................ A61B 1/06
[52] U.S. Cl. ........................................ 128/6; 128/4
[58] Field of Search ......................... 128/4-8, 11; 604/282

[56] References Cited

U.S. PATENT DOCUMENTS

| | | | |
|---|---|---|---|
| 4,236,509 | 12/1980 | Takahashi et al. | 128/4 |
| 4,587,972 | 5/1986 | Morantte, Jr. | 128/660 |
| 4,589,404 | 5/1986 | Barath et al. | 128/6 |
| 4,899,787 | 2/1990 | Ouchi et al. | 138/131 |
| 4,973,321 | 11/1990 | Michelson | 604/280 |
| 4,986,258 | 1/1991 | Cho et al. | 128/7 |
| 5,037,386 | 8/1991 | Marcus et al. | 604/43 |
| 5,048,508 | 9/1991 | Storz | 128/4 |
| 5,058,567 | 10/1991 | Takahashi et al. | 128/4 |
| 5,199,417 | 4/1993 | Muller et al. | 128/6 |

Primary Examiner—John D. Yasko
Assistant Examiner—Adam J. Cermak
Attorney, Agent, or Firm—Gordon L. Peterson

[57] ABSTRACT

An endoscope comprising an elongated endoscope body having a proximal end and a distal end. The endoscope body is sized and adapted for insertion into an interior body region of a patient. Optical components are carried by the endoscope body to enable viewing of the interior body region of the patient. The endoscope body has an outer surface which defines a groove having a portion which extends distally of the endoscope body.

26 Claims, 3 Drawing Sheets

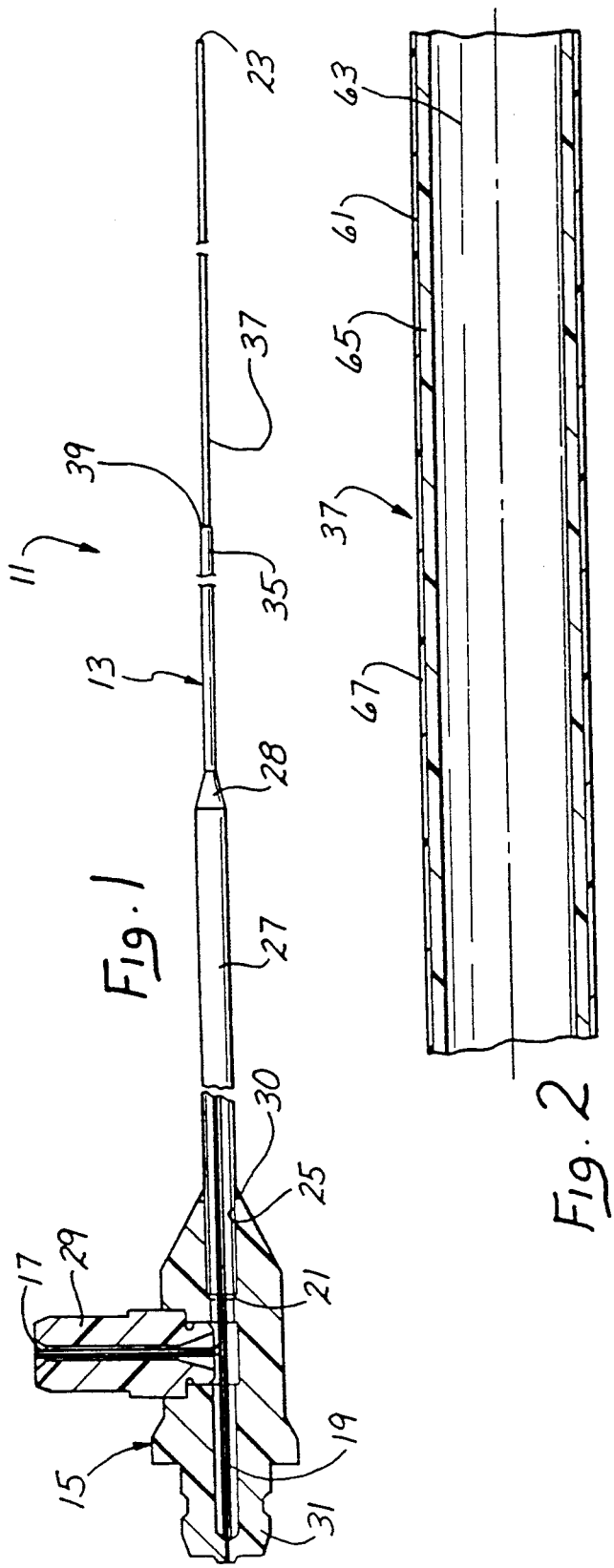
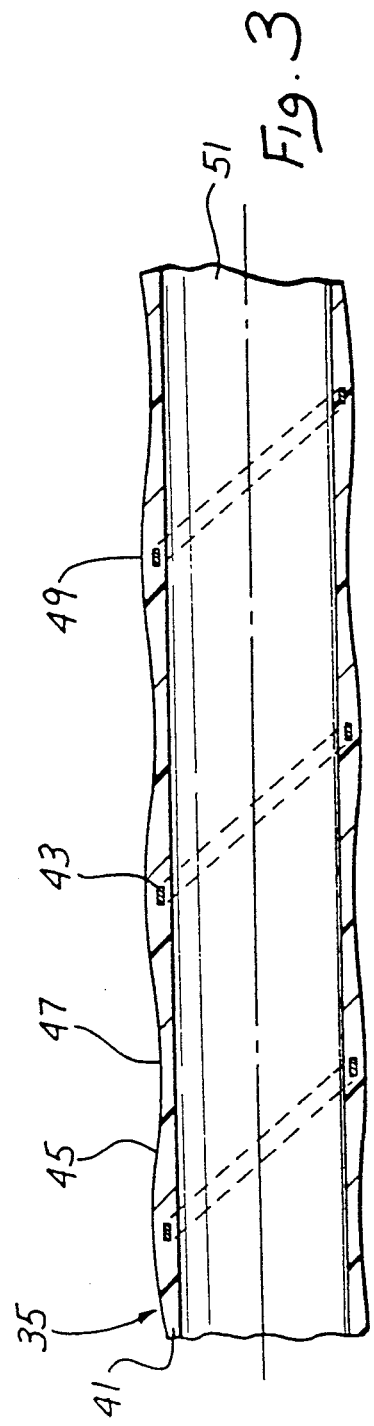

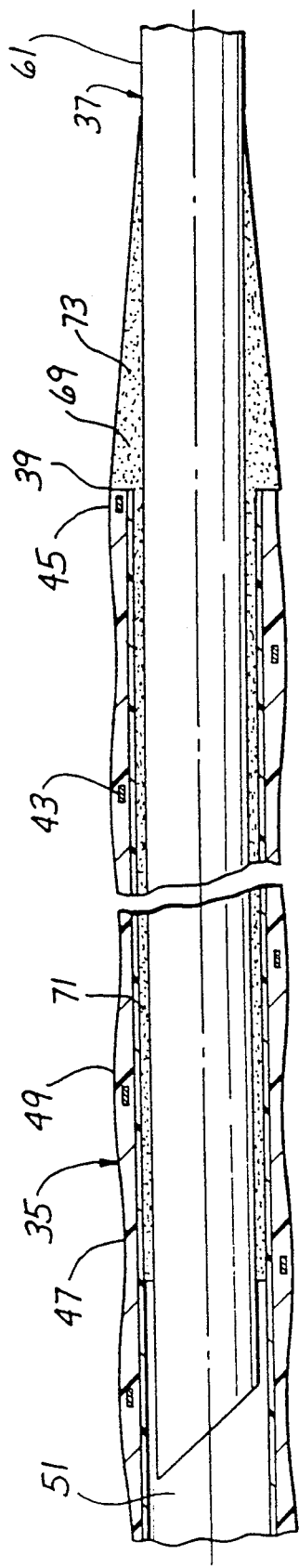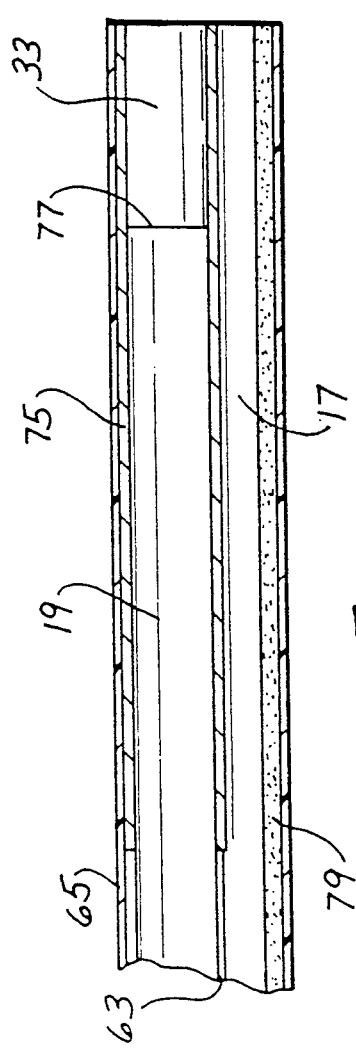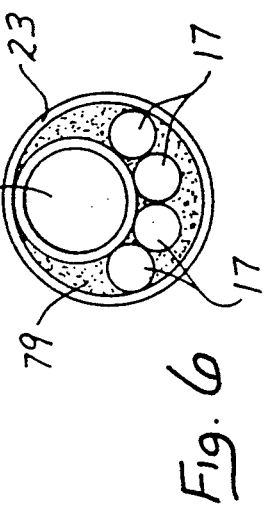

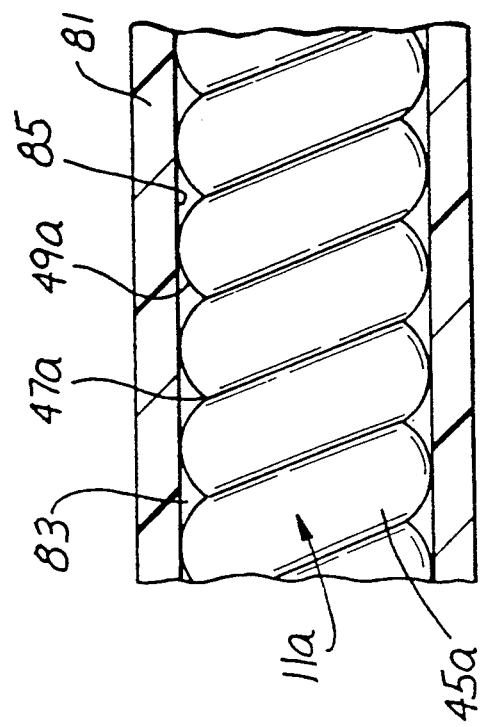
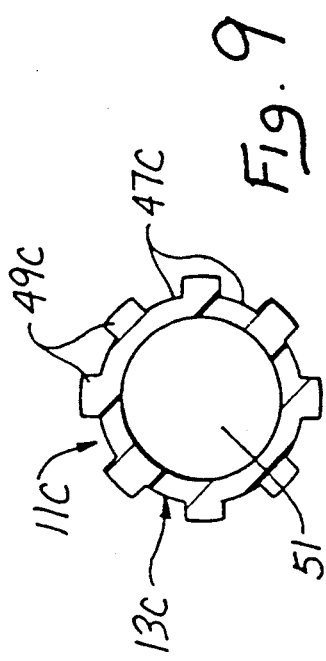
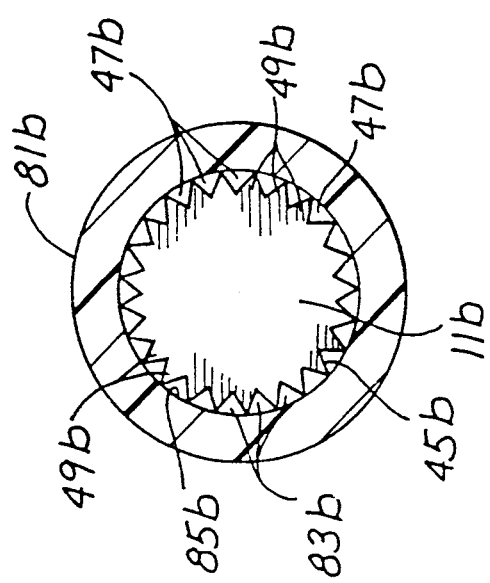

ENDOSCOPE WITH GROOVED OUTER SURFACE

This application is a continuation-in-part of application Ser. No. 780,871 filed on Oct. 18, 1991 and entitled APPARATUS AND METHOD FOR INDEPENDENT MOVEMENT OF AN INSTRUMENT WITHIN A LINEAR EVERSION CATHETER.

BACKGROUND OF THE INVENTION

An endoscope is an instrument which enables a physician to view inaccessible regions within a patient's body. A conventional endoscope may include, for example, an elongated flexible endoscope body and optical components carried by the endoscope body to enable viewing of an interior body region of a patient. The optical components may include, for example, an illumination fiber for illuminating a region to be viewed, an eyepiece and image fibers which transmit an image proximally to the eyepiece.

It is also known to provide an endoscope which has a distal region which is more flexible than a proximal region. The greater stiffness of the proximal region may be the result of reinforcing the proximal region of the endoscope body with, for example, a wire braid.

It is known to provide an endoscope body which includes a polyimide material. Although polyimide provides excellent protection for the optical components within the endoscope body, it does reduce the overall flexibility of the endoscope and may not be as lubricous as desired. Endoscope bodies constructed of polytetrafluoroethylene have the desired lubricity but are generally difficult to bond to other components.

In order for an endoscope to gain access to an interior body region, it often necessary or desirable to pass the endoscope through a catheter, and in some situations, the clearance between the endoscope and the lumen of the catheter through which the endoscope is passed is minimal. This tends to create significant surface area for sliding contact between the endoscope and the catheter thereby making the endoscope more difficult to move relative to the catheter. In addition, it is sometimes necessary or desirable to introduce a liquid, such as a flush solution, through the lumen of the catheter and around the endoscope. The existence of a very small clearance between the endoscope and the catheter makes this task difficult.

It is sometimes desirable to use an endoscope with an everting catheter. An everting catheter typically includes an outer catheter having an outer catheter lumen, an inner catheter movable longitudinally in the outer catheter lumen and having an inner catheter lumen and an everting element coupled to the outer catheter and to the inner catheter. By applying fluid pressure to the everting element and by moving the inner catheter distally in the outer catheter lumen, the everting element can be everted through a distal opening of the outer catheter. The everting element may form an extension of the inner catheter lumen.

The endoscope is positioned within the inner catheter lumen and the extension of the inner catheter lumen. With the instrument so positioned, pressurizing of the everting element causes the everting element to grip a region of the instrument.

This gripping of the instrument by the everting element is useful in that the eversion process may be used to cause the everting element to pull the instrument into the desired body region. Unfortunately, this gripping action is also undesirable to the extent that the physician wishes to move the instrument independently of, and relative to, the everting element.

Parent application Ser. No. 780,871 discloses a method and apparatus which enables the instrument to be moved relative to the everting element of the everting catheter system which includes introducing a flush solution between the everting element and the instrument where the everting element grips the instrument. This frees the instrument from the gripping action of the everting element so the instrument can be moved relative to the everting element. For example, the flush solution can be introduced to a preformed flow passage, i.e. a flow passage that exists even when the everting element grips the instrument. This assures that the flush solution can more easily pass between the everting element and the instrument.

SUMMARY OF THE INVENTION

This invention provides an endoscope which may be used, if desired, to provide a flow passage for flush solution between the endoscope and any surrounding structure. For example, the surrounding structure may be the wall of a catheter lumen which receives the endoscope or the everting element of an everting catheter. In addition, the endoscope of this invention reduces the area of contact between the endoscope and any surrounding catheter structure. The endoscope has features which enable it to be driven more positively by a controller, and the region of the endoscope gripped by the controller may be provided with additional strength to prevent damage to the optical components carried by the endoscope body.

An endoscope constructed in accordance with the teachings of this invention may include an elongated endoscope body having a proximal end and a distal end. The endoscope body is sized and adapted for insertion into an interior body region of a patient. Optical components are carried by the endoscope body to enable viewing of an interior body region of a patient when the endoscope is in the patient.

One feature of this invention is that the endoscope body has an outer surface which defines a groove, at least a portion of which extends distally of the endoscope body. This groove may be used to define or partially define a flow passage when the endoscope is within a catheter and/or when the grooved region of the endoscope is gripped by the everting element of an everting catheter. The groove also reduces the area of contact between the endoscope and any surrounding catheter or body structure and depending on the configuration of the groove may provide a surface irregularity which can be used with advantage to form a positive drive or interlock with the rotating wheels of a controller which may be used for advancing and retracting the endoscope.

The groove may be of any configuration that will enable one or more of these functions to occur. For example, in order for the groove to be used in forming of a flow passage, at least a portion of the groove should extend distally. In a preferred construction, the groove is generally helical and thus extends distally of the endoscope body as it extends around the endoscope body. The helical configuration will also facilitate the gripping of the endoscope by a controller as well as reduce the area of contact between the endoscope and any surrounding catheter structure. There are also advantages in making a structure of this kind as described more fully below.

Alternatively, the groove may extend generally axially. In one preferred construction, there are a plurality of splines on the outer surface of the endoscope body which define a plurality of generally axially extending grooves.

Although this invention is applicable to rigid or flexible endoscopes, it is particularly adapted to flexible endoscopes. The optical components may be of any kind commonly employed in endoscopes such as illumination and visualization fibers.

The endoscope body preferably includes a distal region which includes the distal end and a proximal region which is of larger cross section than the distal region. This construction enables the distal region of the endoscope body to be easily threaded through the opening of a controller and allows the controller to grip and drive the proximal region which has a larger cross sectional area.

The length and location of the groove may be selected in accordance with the functions that are desired. For example, the groove may extend through all, or a portion of, the proximal region and/or the distal region. One advantage of having the groove on the proximal region is that the proximal region is the region gripped by the controller. Accordingly, by providing the groove on the proximal region a more positive drive can be achieved between the controller and the endoscope. Another advantage of locating the groove on the proximal region is that it can provide a flow path between the proximal region and a catheter or other tubular structure through which the proximal region extends.

If the groove is to provide a flow path for flush solution between the everting element of an everting catheter and the endoscope, then the groove is also preferably on the portion of the endoscope gripped by the everting element. Although both the proximal and distal regions of the endoscope may be gripped by the everting element, more commonly it is the distal region that is gripped. In this latter event, it is desirable to provide the groove on the distal region of the endoscope.

Another feature of this invention is to reinforce the proximal region to protect the optical components contained within that portion of the endoscope body particularly when the proximal region is gripped by the controller, such as the controller shown in common assignee's copending application Ser. No. 788,338 filed on Nov. 6, 1991. In a preferred construction, the proximal region includes a polymeric matrix and an elongated, generally helical reinforcing member embedded in the polymeric matrix. This not only reinforces the proximal region of the endoscope body but provides a convenient way for providing the groove on the outer surface of the proximal region of the endoscope body. More specifically, the helical reinforcing member enables the polymeric material to bulge outwardly along a length of the helical reinforcing member to provide a helical rib which defines at least a portion of the groove.

The helical reinforcing member preferably includes a metal coil. The helical reinforcing member can advantageously be in the form of a metal wire of oblong cross section. By orienting the long axis of the oblong cross section generally longitudinally of the endoscope body, good resistance against bending loads is obtained without unduly thickening the wall of the endoscope body.

The distal region can advantageously include a polymeric tube covered with a polymeric layer which provides lubricity. The polymeric layer which provides lubricity may be a fluorinated ethylene propylene, a polytetrafluoroethylene or the like. The polymeric tube provides strength even in thin wall configurations for protecting of the optical components carried within the distal region. A preferred polymeric material for the tube is polyimide. Polyimide is also the preferred polymer for the matrix of the proximal region.

The invention, together with additional features and advantages thereof may best be understood by reference to the following description taken in connection with the accompanying illustrative drawings.

BRIEF DESCRIPTION OF THE DRAWINGS

FIG. 1 is a side elevational view partially in section of one form of endoscope constructed in accordance with the teachings of this invention.

FIG. 2 is a fragmentary axial sectional view through a portion of the distal region of the endoscope with the optical fibers removed.

FIG. 3 is a fragmentary, axial sectional view through a portion of the proximal region of the endoscope with the optical fibers removed.

FIG. 4 is a fragmentary, axial sectional view through the transition region between the proximal and distal regions of the endoscope with the optical fibers removed.

FIG. 5 is a fragmentary, axial sectional view through the portion of the distal region which includes the distal end of the endoscope.

FIG. 6 is an end elevational view of the endoscope.

FIG. 7 is a fragmentary elevational view of a second form of endoscope with the endoscope being illustrated within a tubular structure such as a catheter or other body. The tubular structure is shown in axial cross section.

FIG. 8 is a radial sectional view through either the proximal region or the distal region of a third form of endoscope and tubular structure with the internal details of construction of the endoscope not being illustrated.

FIG. 9 is a radial sectional view through either the proximal region or the distal region of a fourth form of endoscope with the optical fibers removed.

DESCRIPTION OF THE PREFERRED EMBODIMENTS

FIG. 1 shows an endoscope 11 which generally includes an endoscope body 13 and a hub 15. The endoscope 13 also includes one or more illumination fibers 17 (four being illustrated in FIG. 6) and image or visualization fibers 19.

The endoscope body 13 is flexible and has a proximal end 21 and a distal end 23. The proximal end 21 is received within an axial passage 25 of the hub 15. A strain relief tube 27 receives a region of the endoscope body 13 adjacent the proximal end 21 and the strain relief tube is also received within the passage 25. An adhesive 28, such as a urethane adhesive, joins the endoscope body 13 to the tube 27. The endoscope body 13 and the tube 27 are affixed to the hub 15 in any suitable manner, such as by a urethane adhesive 30.

The illumination fibers 17 extend from the distal end 23 through the full length of the endoscope body 13, into the passage 25 and through a leg 29 or illumination connector of the hub 15 which is adapted to be coupled to a light source (not shown). Similarly, the image fibers 19 extend from the distal end 23 through the full length of the endoscope body 13 into the passage 25 and into a leg 31 of the hub 15. A suitable adhesive, such as an epoxy adhesive may be used to bond the ends of the fibers 17 and 19 to the legs 29 and 31, respectively. Although the leg 31 could be adapted for coupling to an eyepiece (not shown) to permit direct visualization, in this embodiment it is adapted for coupling to a camera (not shown) to enable the image to viewed on a monitor. The hub 15 may be constructed of any suitable rigid material with a polymeric material such ABS being preferred.

The optical components of the endoscope 11 may be of any kind which will enable viewing of an interior body region of a patient when the endoscope is in the patient. In the embodiment illustrated in FIGS. 1-6, these optical components include the illumination fibers 17, the image fiber 19 and a GRIN lens 33 (FIGS. 5 and 6) which serves as an objective lens.

The endoscope body 13 includes a proximal region 35 and a distal region 37. The proximal region 35 extends from the proximal end 21 to a transition 39 and the distal region 37 extends from the transition 39 to the distal end 23. For example, the proximal region may be about 60 inches in length and the distal region 37 may be about 14 inches in length. The proximal region 35 is received in and coupled to the hub 15 and a length of the proximal region adjacent the hub is received in the tube 27.

As shown in FIG. 3, the proximal region 35 includes a polymeric matrix 41 and an elongated, generally helical reinforcing member in the form of a coil 43 embedded in the polymeric matrix. Although the polymeric matrix 41 can be constructed of different materials, preferably the polymeric material is a polyimide. Similarly, although the coil 43 can be constructed of different materials, it is preferably constructed of a metal such as stainless steel.

The endoscope body 13 has an outer surface 45 which defines a groove 47, at least a portion of which extends distally of the endoscope body. Although the groove 47 may be of various different configurations, in the embodiment of FIGS. 1-6, the groove 47 is helical. Although the groove 47 may extend for various distances along the outer surface 45, it preferably extends over a major length of the proximal region 35, and in this embodiment, it extends for the full length of the proximal region 35.

The groove 47 is defined by a helical rib 49. By way of example, the outer diameter of the endoscope body as measured at the peak of the rib 49 may be, for example, about 0.0315 inch and the outer diameter of the endoscope body as measured at the bottom of the groove 47 may be about, for example, 0.0285 inch thereby providing a rib height of about 0.0015 inch. Of course, these dimensions are purely illustrative.

The coil 43 is comprised of a stainless steel wire having an oblong cross section with the long axis of the cross section extending generally axially or longitudinally of the endoscope body 13. More specifically, in this embodiment the wire has a rectangular cross section which may be, for example, about 0.001 inch by 0.003 inch.

As shown in FIG. 3, the outer surface 45 of the endoscope body 13 bulges outwardly along a length of the wire forming the coil 43 to provide the helical rib 49. Thus, the coil 43 can be used, not only for reinforcing of the proximal region 35, but also to assist in forming the groove 47. For example, the proximal region 35 can be constructed by dipping of an elongated mandrel (not shown) in the a liquid polyimide and then allowing the polyimide to cure. This dipping step is repeated until the proximal region 35 reaches a desired wall thickness and thereafter, the coil 43 is placed over or wound on the previously formed portion of the matrix 41. Finally, the dipping process referred to above is repeated to form the proximal region 35 substantially as shown in FIG. 3.

The proximal region 35 is elongated, tubular and flexible and has a cylindrical axial passage 51 which is generally cylindrical. Although not shown in FIG. 3, the illumination fiber 17 and the image fiber 19 extend through the passage 51. The outer surface 45 is generally cylindrical, although it does have the groove 47 and the rib 49 as described above. The coil 43 reinforces the proximal region 35 against compressive forces that might damage the fibers 17 and 19 and/or cause signal distortion of the image carried by the image fiber 19. The coil 43 also resists any tendency of the proximal region 35 to kink.

The distal region 37 (FIG. 2) is elongated and flexible and has a generally cylindrical outer surface 61 and a generally cylindrical axial passage 63. Although not shown in FIG. 2, the fibers 17 and 19 extend through the passage 63. The distal region 37 is more flexible than the proximal region 35 and of smaller diameter (FIG. 4). The distal region 37 includes a flexible, cylindrical polymeric tube 65 which defines the passage 63 and which is preferably of polyimide and a coating or layer 67 of a lubricous material, with a polytetrafluoroethylene or a fluorinated ethylene propylene being preferred. The polyimide tube 65 may have a very thin wall thickness which may be, for example, about 0.001 inch. For example, the tube 65 may be extruded or formed in a dipping process and have a diameter of about 0.0185 inch. The layer 67 may, for example, have a diameter of about 0.020 inch and a wall thickness of about 0.00075 inch.

The proximal region 35 and the distal region 37 may be joined at the transition 39 in any suitable manner, although the construction shown in FIG. 4 is preferred. As shown in FIG. 4, a length of the distal region 37 with the layer 67 removed is inserted into the passage 51 of the proximal region 35 and an adhesive 69, such as a cyanoacrylate adhesive, is utilize to bond the region 37 to the region 35. The adhesive 69 includes a tubular section 71 within the passage 51 and a tapered or conical section 73 which is of reducing diameter as it extends distally to blend the outer surface 45 of the proximal region 35 with the outer surface 61 of the distal region 37.

With reference to FIGS. 5 and 6, the lens 33 and a distal region of the image fiber 19 are held by a suitable adhesive, such as an epoxy adhesive, within a lens bushing 75. The lens bushing 75 is constructed of a suitable metal such as stainless steel. The lens 33 is positively coupled to a distal end 77 of the image fiber 19 by a suitable adhesive, which may be an ultraviolet cured adhesive. The lens bushing 75 and the illumination fibers 17 are retained within the passage 63 by a suitable adhesive 79, such as an epoxy adhesive.

Although the endoscope 11 may be adapted to view various interior body regions, in this embodiment it is a falloposcope and is sized and adapted for vaginal insertion into a fallopian tube. This can be accomplished utilizing a catheter, such as an everting catheter as shown by way of example in the parent application.

When in position, the illumination fiber 17 conducts light distally through the distal end 23 and the image fiber 19 conducts an image proximally for visualization either through an eyepiece or by a camera and a monitor. The groove 47 defines or partially defines a flow path for liquids, such as a flush solution when the proximal region 35 is within the lumen of a catheter (not shown) and the reinforced proximal region 35 protects the fibers 17 and 19 from the compressive forces of any controller used to advance and retract the endoscope.

FIG. 7 shows an endoscope 11a which may be identical to the endoscope 11 in all respects not shown or described herein. Portions of the endoscope 11a corresponding to portions of the endoscope 11 are designated by corresponding reference numerals followed by the letter "a".

A primary difference between the endoscopes 11 and 11a is that the endoscope 11a has a helical rib 49a which is more tightly wound than the helical rib 49 to thereby define a helically extending groove 47 which has a helix angle different from the helix angle of the groove 47. In addition, the outer surface 45a is shaped somewhat differently in that the bottom of the groove 47a is not as smoothly curved as in the endoscope 11. As with the endoscope 11, the helical groove 47a and the helical rib 49a may extend over all or portions of the proximal region and/or the distal region.

FIG. 7 also illustrates the endoscope 11a within a tubular structure 81 which may be, for example, a catheter or an everting element of an everting catheter. Regardless of the specific nature of the tubular structure 81, a helical flow passage 83 is defined by the outer surface 45a of the endoscope 11a and an interior surface 85 of the tubular structure 81 which confronts the outer surface 45a. The flow passage 83 assures that flush solution or other liquid will be provided completely around the circumference of the endoscope 11a and extend for the full length of the endoscope which has the helical groove 47a. If the tubular structure 81 is the everting element of an everting catheter, then preferably the helical rib 49a and the helical groove 47a extend over at least a major portion of the proximal region of the endoscope 11a.

FIG. 8 shows an endoscope 11b which may be identical to the endoscope 11 in all respects not shown or described herein. Portions of the endoscope 11b corresponding to portions of the endoscope 11 are designated by corresponding reference numerals followed by the letter "b". The primary difference between the endoscopes 11b and 11 is that the latter has a plurality of axially extending splines or ribs 49b which define a plurality of axially extending grooves 47b on the outer surface 45b of the endoscope 11b. In this embodiment the grooves 47b and ribs 49b are generally triangular in cross section.

The endoscope 11b like the endoscope 11a, is illustrated as being within a tubular structure 81b which has an interior surface 85b which confronts the outer surface 45b of the endoscope 11b. Thus, the flow passage 83b, like the flow passage 83, is defined by confronting surfaces on the endoscope and the tubular structure 81b. Specifically, in FIG. 8 the flow passage 83b is defined by the grooves 47b on the outer surface 45b and the interior surface 85b of the tubular structure 81b. The flow passage 83b extends generally axially. The grooves 47b and the ribs 49b extend along all or portions of the proximal region and/or the distal region of the endoscope 11b.

FIG. 9 shows an endoscope 11c which is identical to the endoscope 11 in all respects not shown or described herein. Portions of the endoscope 11c corresponding to portions of the endoscope 11 are designated by corresponding reference numerals followed by the letter "c".

The endoscope 11c is also identical to the endoscope 11b except for the shape of the ribs 49c and the shape of the grooves 47c. The ribs 49c and grooves 47c are generally rectangular. The endoscope body 13c, like the endoscope body of the endoscope 11b, may be extruded and the ribs 49c may be on all or a portion of the proximal region and/or the distal region of the endoscope body.

Although exemplary embodiments of the invention have been shown and described, many changes, modifications and substitutions may be made by one having ordinary skill in the art without necessarily departing from the spirit and scope of this invention.

We claim:

1. An endoscope comprising:
   an elongated endoscope body having a proximal end and a distal end, said endoscope body being sized and adapted for insertion into an interior body region of a patient;
   optical components carried by the endoscope body to enable viewing of an interior body region of a patient when the endoscope is in the patient;
   said endoscope body having an outer surface which defines a groove, at least a portion of said groove extending distally of the endoscope body; and
   said endoscope body including a distal region which includes said distal end and a proximal region and said groove is on the proximal region and terminates proximally of said distal end.

2. An endoscope as defined in claim 1 wherein said portion of said groove is generally helical.

3. An endoscope as defined in claim 1 wherein said portion of said groove is generally longitudinal.

4. An endoscope as defined in claim 1 including a plurality of splines on the outer surface of the endoscope body defining said groove and a plurality of additional grooves.

5. An endoscope as defined in claim 1 wherein the endoscope body is flexible.

6. An endoscope as defined in claim 1 wherein the optical components include illumination and visualization fibers.

7. An endoscope as defined in claim 1 wherein said proximal region is of larger cross section than the distal region.

8. An endoscope as defined in claim 1 wherein the groove extends over a major length of the proximal region.

9. An endoscope as defined in claim 1 wherein the proximal region includes a polymeric matrix and an elongated, generally helical reinforcing member embedded in the polymeric matrix.

10. An endoscope as defined in claim 9 wherein the polymeric matrix provides the outer surface of at least a portion of the proximal region of the endoscope body and bulges outwardly along a length of the helical reinforcing member to provide a helical rib which defines said portion of said groove.

11. An endoscope as defined in claim 9 wherein the helical reinforcing member includes a metal coil.

12. An endoscope as defined in claim 9 wherein the helical reinforcing member includes a metal wire of oblong cross section with the long axis of the cross section extending generally longitudinally of the endoscope body.

13. An endoscope as defined in claim 1 wherein the distal region includes a polyimide tube and a polymeric layer which is lubricous covering the polyimide tube.

14. An endoscope as defined in claim 1 including a hub, constructed to be coupled to a source of illumination and to a camera, said hub is coupled to the proximal region, and said endoscope including a strain relief tube coupled to the hub and receiving a length of the proximal region adjacent the hub.

15. An endoscope comprising:
an elongated, tubular, flexible endoscope body having a proximal end and a distal end, said endoscope body being sized and adapted for insertion into an interior body region of a patient;
illumination and visualization fibers in the endoscope body for conducting light distally and an image proximally, respectively, of the endoscope body;
the endoscope body including a distal region which includes said distal end and a proximal region of larger cross section than the distal region;
the proximal region of the endoscope body having an outer surface with a generally helical groove; and
said proximal region including a polymeric matrix and an elongated, generally helical reinforcing member embedded in the polymeric matrix.

16. An endoscope as defined in claim 15 wherein the polymeric matrix provides the outer surface of at least a portion of the proximal region of the endoscope body and bulges outwardly along a length of the helical reinforcing member to provide a helical rib which defines at least a portion of said groove.

17. An endoscope as defined in claim 15 wherein the distal region includes a polyimide tube and a lubricous layer covering the polyimide tube.

18. An endoscope comprising:
an elongated endoscope body having a proximal end and a distal end, said endoscope body being sized and adapted for insertion into an interior body region of a patient;
optical components carried by the endoscope body to enable viewing of an interior body region of a patient when the endoscope is in the patient;
the endoscope body including a distal region which includes said distal end and a proximal region of larger cross section than the distal region;
the proximal region includes a polymeric matrix and an elongated, generally helical reinforcing member embedded in the polymeric matrix; and
the distal region includes a polyimide tube and a lubricous polymeric layer covering the polyimide tube.

19. An endoscope as defined in claim 18 wherein the polymeric matrix provides an outer surface of at least a portion of the proximal region of the endoscope body and bulges outwardly along a length of the helical reinforcing member to provide a helical rib which defines at least a portion of a generally helical groove.

20. An endoscope as defined in claim 18 wherein the polymeric matrix is polyimide.

21. An endoscope as defined in claim 18 wherein the lubricous layer comprises a fluorinated ethylene propylene.

22. An endoscope as defined in claim 18 wherein the lubricous layer comprises polytetrafluoroethylene.

23. An endoscope comprising:
an elongated endoscope body having a proximal end and a distal end, said endoscope body being sized and adapted for insertion into an interior body region of a patient;
optical components carried by the endoscope body to enable viewing of an interior body region of a patient when the endoscope is in the patient; and
said endoscope body having an outer surface which defines a helical groove, at least a portion of said groove extending distally of the endoscope body.

24. An endoscope comprising:
an elongated endoscope body having a proximal end and a distal end, said endoscope body being sized and adapted for insertion into an interior body region of a patient;
optical components carried by the endoscope body to enable viewing of an interior body region of a patient when the endoscope is in the patient;
said endoscope body having an outer surface which defines a groove, at least a portion of said groove extending distally of the endoscope body; and
said endoscope including a plurality of splines on the outer surface of the endoscope body defining said groove and a plurality of additional grooves.

25. An endoscope as defined in claim 4 wherein each of said grooves extends generally longitudinally.

26. An endoscope comprising:
an elongated endoscope body having a proximal end and a distal end, said endoscope body being sized and adapted for insertion into an interior body region of a patient;
optical components carried by the endoscope body to enable viewing of an interior body region of a patient when the endoscope is in the patient;
said endoscope body having an outer surface which defines a groove, at least a portion of said groove extending distally of the endoscope body; and
said endoscope body including a distal region which includes said distal end and a proximal region of larger cross section than the distal region and the distal region includes a polyimide tube and a polymeric layer which is lubricious covering the polyimide tube.

* * * * *

UNITED STATES PATENT AND TRADEMARK OFFICE
CERTIFICATE OF CORRECTION

PATENT NO. : 5,279,280
DATED : January 18, 1994
INVENTOR(S) : Bacich et al

It is certified that error appears in the above-identified patent and that said Letters Patent is hereby corrected as shown below:

Column 10, line 37 change "claim 4" to -- claim 24 --.

Signed and Sealed this

Nineteenth Day of July, 1994

Attest:

BRUCE LEHMAN

*Attesting Officer*  *Commissioner of Patents and Trademarks*